(12) United States Patent
Moriwaki et al.

(10) Patent No.: US 8,017,380 B2
(45) Date of Patent: Sep. 13, 2011

(54) REAL-TIME PCR SYSTEM

(75) Inventors: Toshiki Moriwaki, Kanagawa (JP);
Tasuku Yotoriyama, Tokyo (JP); Yuji Segawa, Tokyo (JP)

(73) Assignee: Sony Corporation, Tokyo (JP)

( * ) Notice: Subject to any disclaimer, the term of this patent is extended or adjusted under 35 U.S.C. 154(b) by 677 days.

(21) Appl. No.: 12/105,722

(22) Filed: Apr. 18, 2008

(65) Prior Publication Data

US 2008/0280350 A1    Nov. 13, 2008

(30) Foreign Application Priority Data

May 11, 2007    (JP) ................. 2007-126344

(51) Int. Cl.
*C12Q 1/68* (2006.01)
*C12M 1/36* (2006.01)
*C12M 1/38* (2006.01)
*C12M 3/00* (2006.01)
*C12M 1/34* (2006.01)

(52) U.S. Cl. .... 435/287.1; 435/6; 435/286.1; 435/287.2

(58) Field of Classification Search ........... 435/6, 286.1, 435/287.1, 287.2
See application file for complete search history.

(56) References Cited

U.S. PATENT DOCUMENTS

| | | | |
|---|---|---|---|
| 6,504,226 | B1 | 1/2003 | Bryant |
| 6,864,140 | B2 | 3/2005 | Bryant |
| 2003/0008286 | A1 | 1/2003 | Zou et al. |
| 2003/0116552 | A1 | 6/2003 | Santoruvo et al. |
| 2003/0119289 | A1 | 6/2003 | Bryant |
| 2005/0221373 | A1* | 10/2005 | Enzelberger et al. ............. 435/6 |
| 2006/0061406 | A1 | 3/2006 | Takatori |
| 2006/0073491 | A1* | 4/2006 | Joseph et al. ...................... 435/6 |
| 2006/0228268 | A1* | 10/2006 | Heimberg et al. ............ 422/130 |
| 2007/0212681 | A1* | 9/2007 | Shapiro et al. .................... 435/5 |
| 2007/0284360 | A1 | 12/2007 | Santoruvo |
| 2009/0169190 | A1* | 7/2009 | Fang et al. .................... 392/485 |

FOREIGN PATENT DOCUMENTS

| | | |
|---|---|---|
| EP | 1 541 237 | 6/2004 |
| JP | 2003-298068 | 10/2003 |
| JP | 2004-025426 | 1/2004 |
| WO | 03/075111 | 9/2003 |
| WO | 2005/118773 | 12/2005 |
| WO | 2007/034437 | 3/2007 |
| WO | 2007/094744 | 8/2007 |
| WO | 2007/107910 | 9/2007 |

* cited by examiner

*Primary Examiner* — Robert J Warden
(74) *Attorney, Agent, or Firm* — K&L Gates LLP (57) ABSTRACT

A real-time PCR system for detecting gene expression levels includes plural reaction regions, a like plural number of heating portions arranged corresponding to the reaction regions and having heat sources, respectively, an optical unit capable of irradiating exciting light of a specific wavelength to all of the plural reaction regions, and a like plural number of fluorescence detecting portions arranged corresponding to the reaction regions, respectively. The heating portions are each provided with a temperature detector for detecting a temperature in a vicinity of the corresponding heat source and converting the temperature into an electrical signal and also with a controller for controlling a thermal dose from the corresponding heat source based on a correlation between electrical signals and calorific values of the heat source stored beforehand.

7 Claims, 6 Drawing Sheets

REAL-TIME PCR SYSTEM

CROSS REFERENCES TO RELATED APPLICATIONS

The present application claims priority to Japanese Patent Application JP 2007-126344 filed in the Japan Patent Office on May 11, 2007, the entire contents of which being incorporated herein by reference.

BACKGROUND

The present application relates to a real-time PCR system. More specifically, the present application is concerned with a real-time PCR system for assaying gene expressions and the like.

In recent years, hybridization detection technologies led by DNA chips and DNA microarrays have been finding increasing practical applications. A DNA chip includes a wide variety of DNA probes integratedly immobilized on a surface of a substrate. By detecting, with this DNA chip, hybridizations on the surface of the substrate in the DNA chip, gene expressions in cells, a tissue or the like can be comprehensively assayed.

It has now become a standard method for the quantitative assay of trace nucleic acids to verify, by PCR (polymerase chain reaction), data acquired by such a microarray.

Real-time PCR can amplify DNA or the like to several hundred thousand-fold by continuously performing amplification cycles of "thermal denaturation→annealing with a primer→polymerase extension reaction". Real-time PCR monitors the resulting PCR amplification products in real time to perform a quantitative assay of the trace nucleic acids.

According to real-time PCR, the PCR amplification products can be monitored using a dedicated system or the like with a thermal cycler and a fluorescence spectrophotometer combined together as an integral unit. As such systems, there are real-time PCR systems.

A real-time PCR system is a reaction and processing system that upon allowing amplification to proceed through reactions in a sample, irradiates exciting light and detects fluorescent signals in real time. It can be used as a detection system or the like to conduct genome DNA observations in medical care practice and gene analysis studies, including chemical reactions.

When labeling is conducted with a fluorescent dye to specify a double-stranded DNA of interest to be synthesized, for example, in a PCR method that amplifies DNAs, heating of the double-stranded DNA makes it possible to observe variations in intensity of fluorescence to be emitted from the florescent dye.

When only a target DNA of interest can be amplified with a high-specificity primer, for example, intercalation making use of "SYBRR™ GREEN I" (product of Molecular Probe, Inc.) can be used.

An intercalator, which is used emit fluorescence upon binding to a double-stranded DNA, binds to a double-stranded DNA synthesized by a PCR reaction, and emits fluorescence when exciting light is irradiated. By detecting the intensity of this fluorescence, the amount of the amplification product can be monitored. Intercalation, therefore, does not require design and synthesize a fluorescently-labeled probe specific to the target DNA, and can be easily used in the assay of various target DNAs.

Further, the probe method is used when there is a need to separately detect sequences which are very close to each other or when a multiplex detection is needed as in SNP typing. As one example of the probe method, there is the "TAQMAN™ PROBE" method (product of Applied Biosystems, Inc.) which uses as a probe an oligonucleotide modified at the 5' terminal with a fluorescent material and at the 3' terminal with a quencher material.

"TaqMan™ probe" specifically hybridizes with a template DNA in an annealing step. Due to the existence of a quencher on the probe, however, the emission of fluorescence is inhibited even when exciting light is irradiated. In an extension reaction step, the "TAQMAN PROBE" hybridized on the template is decomposed by the 5'→3' exonuclease activity of TaqDNA polymerase, the fluorescent dye is liberated from the probe, the inhibition by the quencher is cancelled, and therefore, fluorescence is emitted. By measuring the intensity of this fluorescence, the amount of the resulting amplification product can be monitored.

A description will hereinafter be made of the principle of a quantitative assay of a gene expression level or abundance by real-time PCR in the above-described manner. Firstly, PCR is performed using as templates serially-diluted standard samples the concentrations of which are known. Numbers of cycles (threshold cycles: Ct values) required to each a certain constant amount of amplification product are then determined. A calibration line is then prepared by plotting these Ct values and initial DNA amounts along the abscissa and the ordinate, respectively.

With respect to a sample the concentration of which is unknown, a PCR reaction is also conducted under the same conditions to determine a Ct value. From this Ct value and the above-mentioned calibration line, the amount of the target DNA in the sample can be determined.

As techniques relating to the above-described real-time PCR, technologies on temperature control or the like are disclosed in Japanese Patent Laid-open Nos. 2003-298068 and 2004-025426.

SUMMARY

Such PCR systems are characterized by excellent quantitative capability in the detection of gene expression levels. They are, however, accompanied by a problem in that many samples cannot be assayed together at the same time and hence, no comprehensive assay is feasible. Temperature control by a thermal cycler or the like commercially available nowadays is dependent on a gradient system, so that samples cannot be controlled independently in temperature. As a consequence, there are problems that the amplification levels of the individual samples cannot be controlled to be equal to each other and byproducts may occur.

The present application, therefore, has as a primary object thereof the provision of a real-time PCR system, which can perform a comprehensive assay and can effect temperature control of each reaction region with high accuracy.

In one embodiment, there is thus provided a real-time PCR system for detecting gene expression levels, comprising: plural reaction regions, a like plural number of heating portions arranged corresponding to the reaction regions and having heat sources, respectively, an optical unit capable of irradiating exciting light of a specific wavelength to all of the plural reaction regions, and a like plural number of fluorescence detecting portions arranged corresponding to the reaction regions, respectively, wherein the heating portions are each provided with a temperature detector for detecting a temperature in a vicinity of the corresponding heat source and converting the temperature into an electrical signal and a controller for controlling a thermal dose from the corresponding heat source based on a correlation between electrical signals and calorific values of the heat source stored beforehand. Owing to the arrangement of the heating portions for the respective reaction regions and also owing to the detection of temperatures in the vicinities of the heat sources in the respective heating portions, the conversion of the temperatures into electrical signals, the advance storage of a correlation between the electrical signals and calorific values of the heat sources and the feedback of the correlation to heat treatment, the heating can be controlled with high accuracy.

The temperature detector of each heating portion can use a thin-film transistor (TFT: thin film transistor) or EL (electroluminescence) device as a detection medium.

The controller for controlling the thermal dose from each heat source can be provided with a temperature control circuit, and the temperature detector can comprise a detection medium arranged in the temperature control circuit. This embodiment makes it possible to further downsize the real-time PCR system as a device and also to systematically control the detection of temperatures and the control of the heat sources.

The temperature detector can comprise an EL device as a detection medium, the controller for controlling the thermal dose from the heat source can comprise a thin-film transistor as a control medium, and the EL device and the thin-film transistor can be arranged in a same pixel circuit. By arranging the temperature detection medium and the heat control medium in the same pixel as described above, the real-time PCR system can be further downsized as a device.

The heating portions can each be further provided with a Peltier element which enables constant-temperature control. The Peltier element can perform constant-temperature control of the corresponding heating portion, so that a reaction in the corresponding reaction region can be controlled with higher accuracy.

According to the real-time PCR system of the present application, gene expression levels can be controlled with high accuracy.

Additional features and advantages are described herein, and will be apparent from the following Detailed Description and the figures.

DETAILED DESCRIPTION

Preferred embodiments of the real-time PCR system according to the present application will hereinafter be described with reference to the accompanying drawings. It is to be noted that the drawings illustrate the preferred embodiments of the present application by way of example and that the present application shall not be construed as the preferred embodiments.

Figure 1:
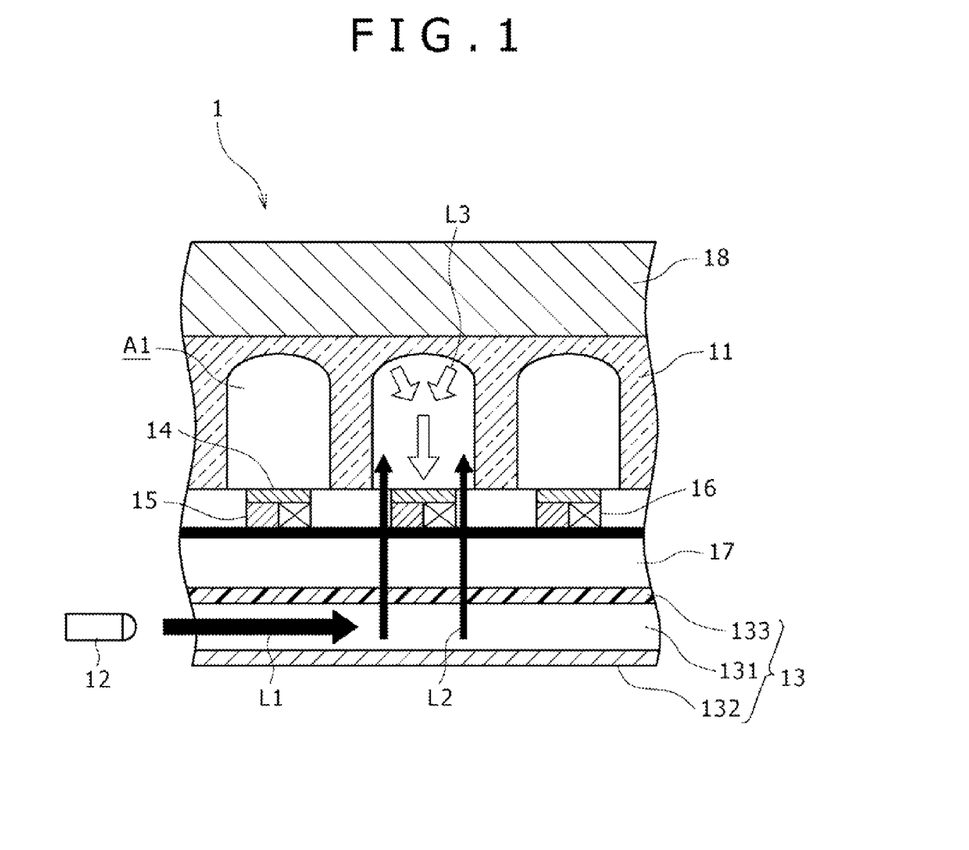
FIG. 1 is a fragmentary conceptual diagram of a first embodiment of the real-time PCR system according to the present application as viewed in side elevational cross-section.

Referring firstly to FIG. 1, a description will hereinafter be described of the first embodiment of the real-time PCR system.

Designated at numeral 1 in FIG. 1 is the first embodiment of the real-time PCR. The size and layer structure of the real-time PCR system 1 can be selectively determined, as desired, depending on an application purpose. The configuration of the real-time PCR system 1 can also be designed or modified as desired insofar as the real-time PCR system 1 can achieve the object of the present application.

The real-time PCR system 1 is provided with a well substrate 11 defining plural reaction regions A1 therein, a light source 12, and an exciting-light scanning plate 13 for guiding exciting light L1, L2 emitted from the light source 12. In addition, filters 14, fluorescence detectors 15 for detecting fluorescence L3, and heaters 16 for heating the reaction regions A1, respectively, are arranged on a measuring substrate 17.

In the real-time PCR system 1, the exciting light L1 emitted from the light source 12 is guided through the exciting-light scanning plate 13, and is then irradiated as the exciting light L2 into each reaction region A1. The light L3 emitted from the reaction region A1 is then detected and measured by the corresponding fluorescence detector 15.

The real-time PCR system 1 of the first embodiment is characterized especially in that the each reaction region A1 is provided with the corresponding heating portion 16 and also that the heating portion 16 is provided with a temperature detector for detecting a temperature in a vicinity of a heat source of the heating portion 16 and converting the temperature into an electrical signal and also with a controller for controlling a thermal dose from the heat source based on a correlation between electrical signals and calorific values of the heat source stored beforehand. The real-time PCR system 1 can, therefore, control the temperatures of the individual heating regions A1 independently with high accuracy. It is to be noted that the calorific value of each heat source can be estimated by measuring, for example, its exothermic temperature. The individual elements of the real-time PCR system will hereinafter be described in detail.

The well substrate 11 is provided with the plural reaction regions (well) A1. Predetermined reactions are to be performed in these reaction regions A1, respectively. The well substrate 11 can be formed, for example, with a low-fluorescence plastic material or glass material, and the reaction regions A1 can be arrayed as many as the human genome number in a matrix.

The reaction regions (wells) for PCR reactions may desirably be in the form of microcavities. When wells are each dimensioned as small as 300 µm×300 µm×300 µm (capacity: approx. 30 nL) and such wells are arrayed as many as about 40,000 wells, for example, the resulting device will have an area of about 6 cm squares.

No particular limitation is imposed on the shape of each reaction region 1, and each reaction region 1 may be in any form insofar as it can retain a reaction mixture. A desired suitable shape can be chosen while taking into consideration the light path through which the exciting light L1, L2 is introduced and irradiated, the light path for detecting the fluorescence L3, etc. As the real-time PCR system 1 requires to have the fluorescence L3 reflected in each reaction region A1, each reaction region A1 is provided with a curved surface area.

To inhibit a reduction in detection sensitivity due to influence of light scattering and outside light, the reaction regions A1 may desirably be coated with a light-shielding material (for example, diamond-like carbon or the like).

This first embodiment uses the light source 12 and the exciting-light scanning plate 13, which introduces the exciting light L1 into each of the plural reaction regions A1, as optical means capable of irradiating exciting light of specific wavelength into all the reaction regions A1.

No particular limitation is imposed on the type of the light source 12 insofar as light of the specific wavelength can be emitted. Preferably, a white or monochromatic light-emitting diode (LED) can be used. The use of such a light-emitting diode makes it possible to easily obtain light which does not include unnecessary ultraviolet ray or infrared ray.

No particular limitation is imposed on the installation place of the light source 12 or the number of such light source(s). Although not illustrated in the figure, it is possible to adopt such an architecture that plural light sources are arranged corresponding to the respective reaction regions A1 to irradiate exciting light from the individual light sources directly toward their corresponding reaction regions A1. This architecture makes it possible to directly irradiate each reaction region A1 by its corresponding light source, so that the exciting light can be irradiated in a larger quantity and moreover, the quantities of the exciting light L1, L2 can independently controlled. The exciting light L1, L2 can, therefore, be irradiated at the equal level into the respective reaction regions A1.

The exciting-light scanning plate 13 serves to guide the exciting light L1, which has been emitted from the light source 12, into each reaction region A1 in the well substrate 11. The exciting light L1 emitted from the light source 12 is introduced into a spacer 131 formed inside the exciting-light scanning plate 13. A reflective film 132 is arranged in a lower part of the light-exciting scanning plate 13, so that the exciting light L2 can be guided into the well substrate 11. As a consequence, a fluorescent material on a probe in the reaction mixture within each reaction region A1 can be excited by the equal quantity of exciting light. No particular limitation is imposed on the material of the reflective film 132. Desirably, however, a dichroic mirror can be used.

In this first embodiment, a filter 133 which transmits only light of the wavelength of the exciting light L1, L2 may desirably be arranged in an upper part of the exciting-light scanning plate 13. The filter 133 makes it possible to efficiently extract the exciting light L2 from the light emitted from the light source 12 and to guide the same into the respective reaction regions A1. As this filter 133, a polarizing filter or the like can be used, for example.

To the exciting light L2 irradiated into each reaction region A1, the fluorescent material on the probe in the reaction mixture is exposed, and therefore, the fluorescence L3 is produced. This fluorescence L3 is reflected at a wall inside the reaction region A1, and is detected and measured at the fluorescence detector 15 arranged below the reaction region A1.

In this first embodiment, it may be preferred to also arrange the filter 14 between each reaction region A1 and its corresponding fluorescence detector 15 to permit extraction of light of specific wavelength. No particular limitation is imposed on the material of the filter 14 insofar as light of specific wavelength (fluorescence L3 can be extracted. For example, a dichroic mirror can be used.

Each fluorescence detector 15 detects and measures fluorescence emitted as a result of excitation of the fluorescent material on the probe intercalated responsive to the exciting light L2 irradiated into the corresponding region A1.

In the real-time PCR system 1, the reaction regions A1 are provided with the heating portions 16, respectively. Each heating portion 16 is provided with a temperature control system, which performs temperature control of the corresponding reaction region A1. When performing PCR cycles, for example, the temperature control system makes it possible to effect temperature control with higher accuracy with respect to the "thermal denaturation→annealing→extension reaction" steps in each cycle.

A description will hereinafter be made about the temperature detector for each heating portion 16 and the controller for the thermal dose from its heat source.

In this first embodiment, each heat detector is arranged in the vicinity of the heat source of its corresponding heating portion 16. As the temperatures in the vicinities of the respective heat sources can be separately detected, minute temperature changes in the respective reaction regions A1 can be detected. For the detection, it is possible to use a method that converts each detected temperature into an electrical signal.

In the first embodiment, the correlation between electrical signals and calorific values of the heat source is stored beforehand, and the thermal dose from each heat source is controlled using this correlation. As a consequence, the thermal dose from each heat source can be controlled based on temperature information detected by the temperature detector.

As a method for controlling the thermal dose from the heat source of each heating portion 16, it is possible to use, for example, a method that subjects a correlation between a calorific value by a heat control/generation current at each heat source and a preset index temperature to feedback control in real time.

Figure 2:
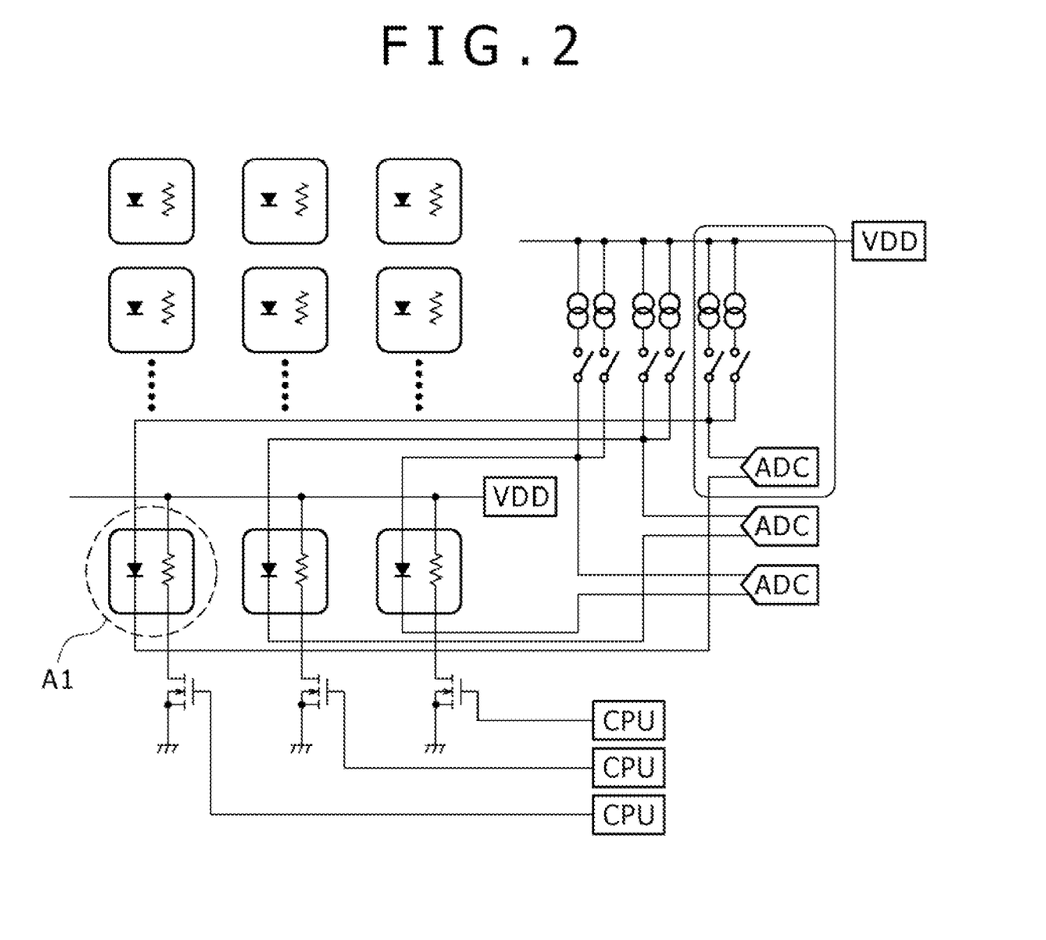
FIG. 2 is a fragmentary conceptual circuit diagram of one example of the first embodiment, in which each heating portion is provided with its own temperature detection system and heat source.

Referring next to FIG. 2, the heating portions 16 will be described more specifically. In FIG. 2, the temperature detection system and heat source are arranged corresponding to each reaction region A1. Detected temperature information (a temperature in the vicinity of the heat source) is outputted to an ADC (analog-digital converter). Based on this information, computation is then performed at a CPU arranged corresponding to the reaction region A1. As a result, information on an adequate thermal dose to the reaction region A1 is transmitted to the corresponding heat source.

Figure 3:
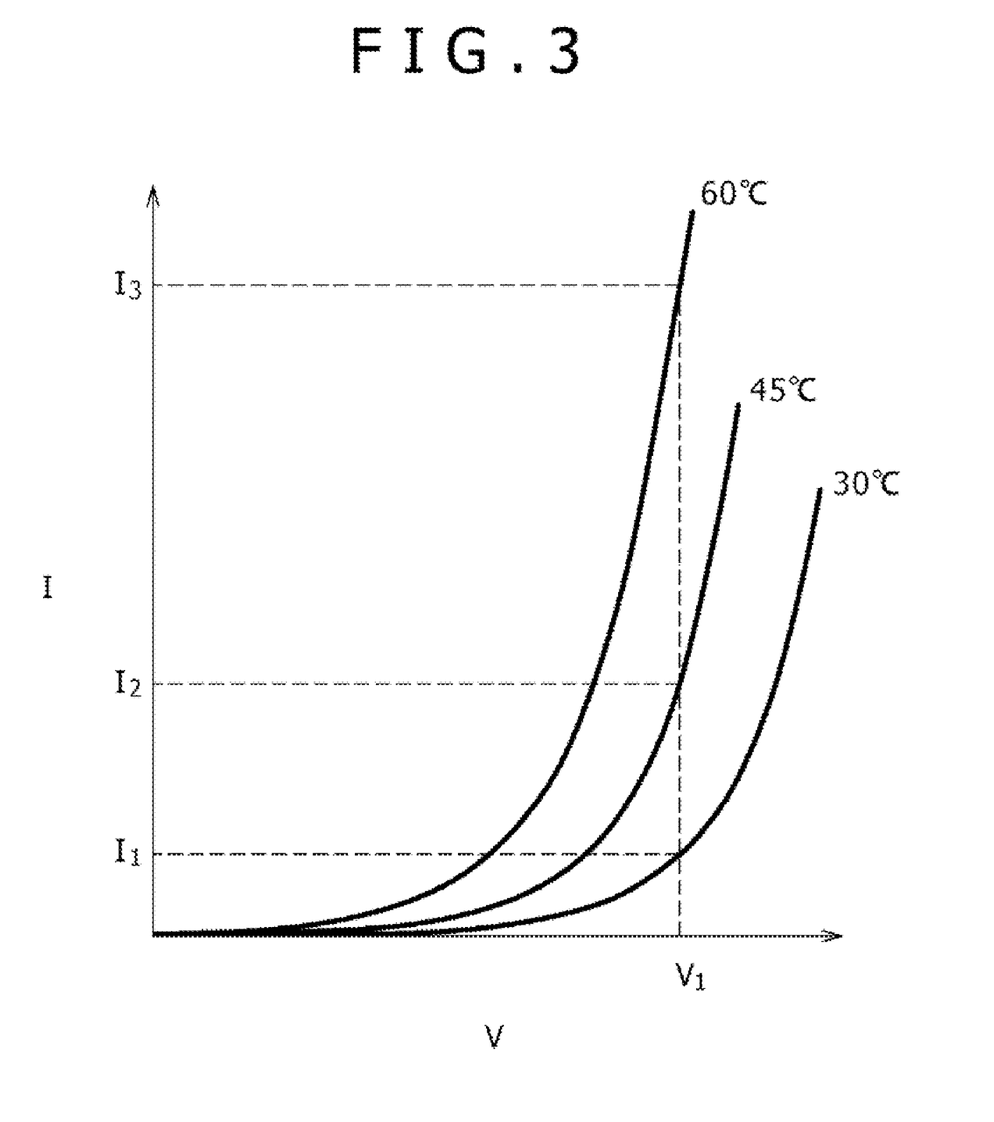
FIG. 3 is a diagram illustrating one example of a correlation among current values, voltage values and temperatures.

The temperature detector for each heating portion 16 in this first embodiment has the temperature detector, which detects a temperature in the vicinity of the corresponding heat source and converts it into an electrical signal (current value or voltage value). As a device useful as a detection medium for the temperature detector in the above-described temperature control, a device having diode characteristics or a like device can be mentioned. Such a device (for example, a thin-film transistor, EL device or the like) is equipped with characteristics having such a correlation between electrical signals (current values or voltage values) and temperatures as shown in FIG. 3.

A thin-film transistor, EL device or the like, which is equipped with diode characteristics, has characteristics that an applied current value at a constant voltage or a drive voltage at a constant current varies depending on the temperature. When a constant voltage V1 is applied, for example, an applied current value I1 is detected when the actual temperature is 30° C., an applied current value I2 is detected when the actual temperature is 45° C., and an applied current value I3 is detected when the actual temperature is 60° C. (see FIG. 3). When a drive voltage is similarly measured while controlling a current constant, the voltage value can be detected to vary depending on the actual temperature.

As the detection medium for the temperature detector arranged in the vicinity of each heat source, a device equipped with diode characteristics can be used as described above. Preferably, a thin-film transistor, EL device or the like can be used.

No particular limitation is imposed on the type of the thin-film transistor. For example, a thin-film transistor of polysilicon, α-silicon or the like can be used as desired.

An EL device is equipped with characteristics that a drive voltage at a constant current or an applied current value at a constant voltage varies depending on the temperature. By using these characteristics, the EL device can detect the above-described temperature information as an electrical signal.

Figure 4:
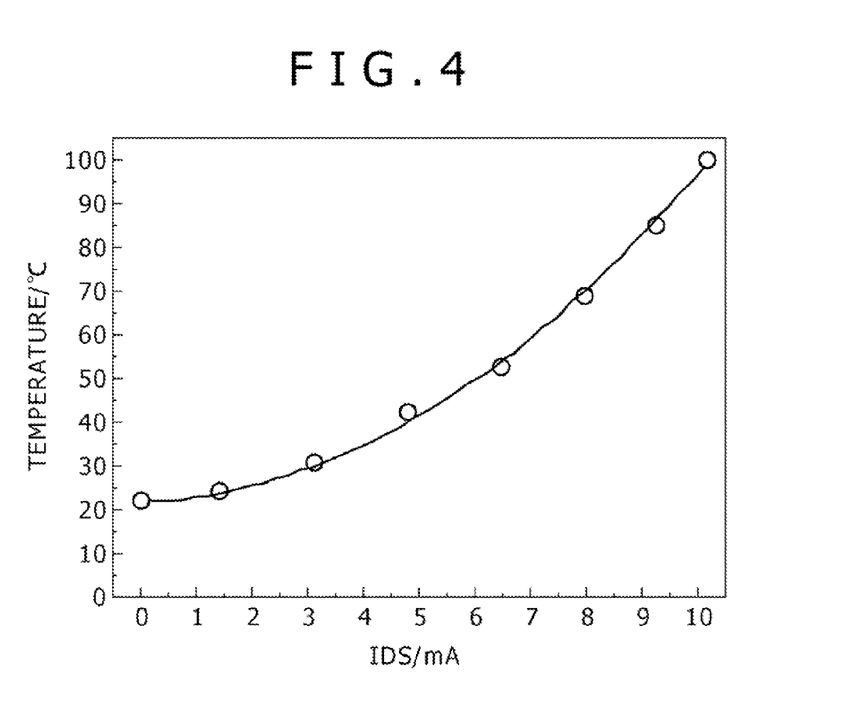
FIG. 4 is a diagram showing one example of a correlation between control temperature values and temperatures.

Between drain (D)-source (S) current values (Ids) and heating temperatures, there is a certain specific correlation as illustrated in FIG. 4. By storing this correlation as a correspondence table or the like in the corresponding control medium, the control current or the like can be controlled. As a result, the thermal dose from each heat source can be controlled with high accuracy. Further, the control current or the like can be set to correct the thermal dose.

This first embodiment may be provided with a means for correcting a thermal dose to each heating portion 16 on the basis of a pre-obtained correlation between electrical signals and calorific values produced by the corresponding heat source. When the thermal dose is corrected, for example, based on a physical value produced corresponding to a temperature detected by a temperature detection system, the control current is controlled based on a pre-stored correspondence table (correlation) between electrical signals and temperatures. A high-accuracy temperature control cycle system can be obtained accordingly.

Figure 5:
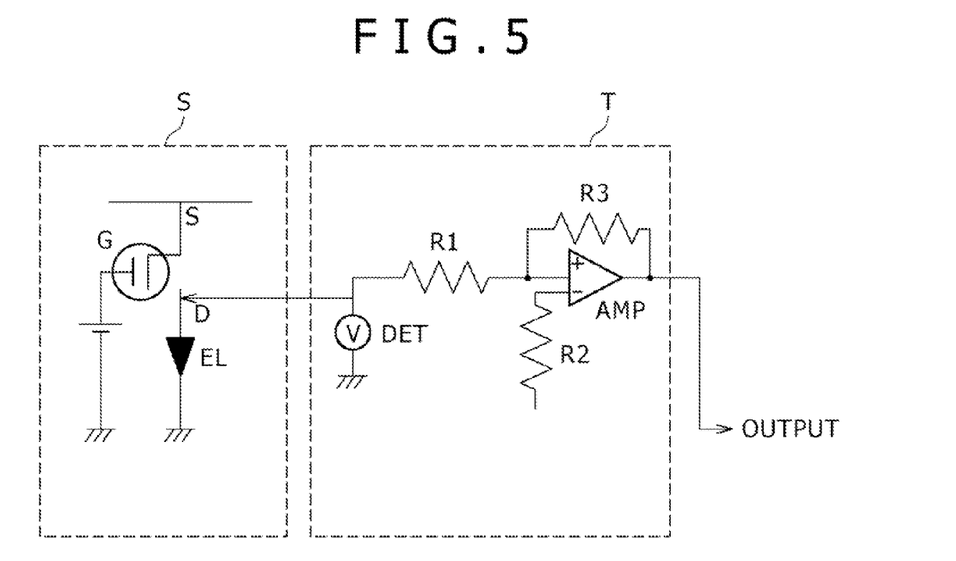
FIG. 5 is a circuit diagram depicting one example of a circuit of the temperature detection system of each heating portion.

With reference to FIG. 5, one example of the temperature detection system for each heating portion 16 will hereinafter be described. The temperature detection system is composed of a section S and a section T. The section S performs the detection of a temperature in the vicinity of the heat source, while the section T makes up a voltage level control circuit. A load resistance is connected in series to an EL device which performs the detection of a current value/voltage value shift (the detection of a variation quantity in electrical signal) to detect a temperature.

In addition, a thin-film transistor (source: S) with a constant voltage being applied to its gate G is used. By this construction, a sufficiently high voltage is applied between a cathode of the EL device and the source of the thin-film transistor.

A resistor R1 is connected to a connection contact between the EL device and the load resistance. A voltage detected at the EL device is applied to a non-inverting input terminal (+) of a differential amplifier (AMP). A resistor R2 is connected to an inverting input terminal (−) of the differential amplifier (AMP), and a resistor R3 is arranged between the non-inverting input terminal (+) and an output terminal of the differential amplifier (AMP). Therefore, the voltage detected at the EL device is amplified by a predetermined gain and is outputted.

Figure 6:
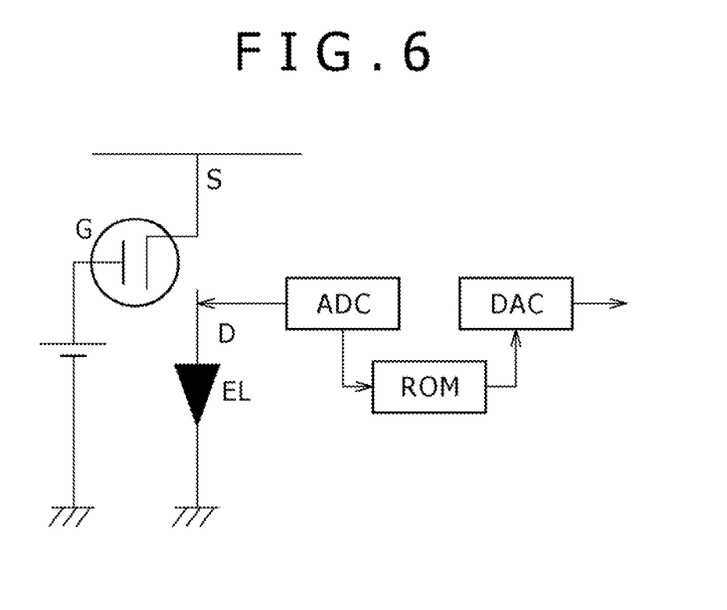
FIG. 6 is a circuit diagram illustrating another example of the circuit of the temperature detection system of the heating portion.

Referring next to FIG. 6, another example of the temperature detection system for each heating portion 16 will be described. The above-described temperature detection system shown in FIG. 5 can be simplified, for example, like the pixel circuit illustrated in FIG. 6. Described specifically, FIG. 6 depicts a construction that as a replacement for the section T (voltage level control circuit, see FIG. 5), a temperature difference is detected based on linear data (for example, gains) stored in a ROM via an analog-digital converter (ADC). This temperature difference detection data is then outputted to a digital-analog converter (DAC). This method can use the linear data stored beforehand in the ROM, and therefore, can use more precise temperature difference detection data.

In this first embodiment, the heating time of each reaction region A1 can also be independently controlled by its corresponding heating portion 16. Amplification reactions or the like in the respective reaction regions A1 can, therefore be independently controlled with high accuracy by controlling the heating temperature and heating time independently from one reaction region to another.

Figure 7:
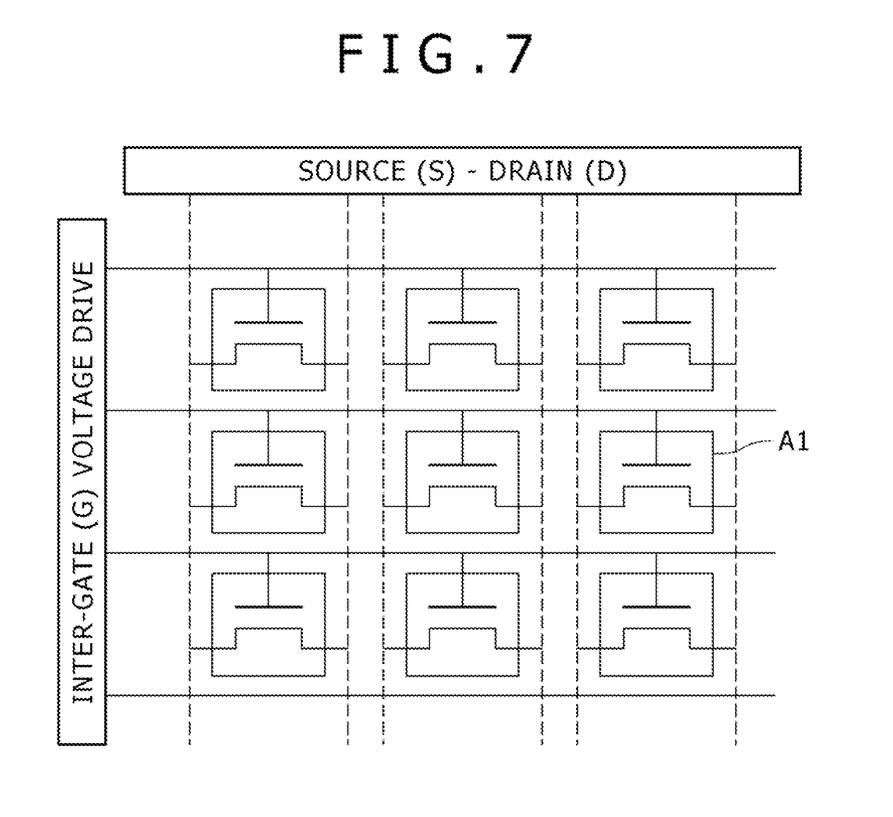
FIG. 7 is a conceptual diagram showing by way of example heating portions arrayed, in a matrix, corresponding to respective reaction regions.

As depicted in FIG. 7, the heating portions 16 can be arrayed in a matrix based on the respective reaction regions A1.

Described specifically, the heating portions 16 can be arranged corresponding to the reaction regions A1 such that the heating portions 16 are arrayed in a matrix along gate lines (X-direction) and data lines (Y-direction). The temperature detection in the vicinities of the heat sources of the respective heating portions 16 and the control (heat control) of thermal doses from the respective heat sources can be systematically controlled.

It is, therefore, desired to arrange the detection media, which are employed in the respective temperature detectors, in the circuits for controlling thermal doses from the corresponding heat sources. The adoption of such construction enables to downsize the device. As a result, a comprehensive assay can be efficiently performed although the real-time PCR system is a small device. Further, the above construction makes it possible to omit an irksome fabrication step which would otherwise be required in general.

More desirably, the detection medium for use in the temperature detector in the vicinity of each heat source can be an EL device, the control (heat control) of the calorific value of each heating portion 16 can be performed by a thin-film transistor, and the EL device and the thin-layer transistor can be arranged in the same pixel circuit.

The incorporation of the EL device and thin-film transistor in the same pixel circuit is preferred, because the temperature detection and the heat control can be systematically controlled and space saving is feasible.

The detection media for use in the respective temperature detectors and the detection media for controlling thermal doses from the respective heat source can be formed into a stacked structure with a protective layer interposed between the former detection media and the latter detection media. As this stacked construction permits further space spacing, the real-time PCR system can be fabricated as a still smaller device.

Although not illustrated in the figure, a pixel circuit of a fluorescence detector useful for each fluorescence detector 15 and a pixel circuit of a control medium for the control of a thermal dose from the corresponding heat source can be arranged in the same pixel. As the internal architecture of the same pixel, the temperature controller and the fluorescence detector may be formed into a stacked structure with a protective layer interposed between them.

As a consequence, heat control and fluorescence detection can be performed in the same pixel layer, and moreover, downsizing as a device can be materialized more easily. For example, the pixel circuits of the thin-film transistors and EL devices for the respective fluorescence detectors 15 can be arranged in the pixel circuits of the heat-controlling thin-film transistors and EL devices for the respective heating portions 16.

Desirably, a Peltier element 18 can be arranged to perform temperature control of the respective reaction regions A1. PCR cycles require to perform temperature control corresponding to the steps of "thermal denaturation→annealing (hybridization using primers)→extension reaction". The arrangement of the Peltier element 18 can further facilitates constant-temperature control and can perform high-accuracy temperature control. For example, the temperature in each reaction region A1 can be maintained beforehand at a lowest temperature (for example, 55° C.) in PCR cycles.

With the real-time PCR system 1 according to the first embodiment, commonly-employed PCR methods can be performed. Described specifically, a target DNA can be amplified to a desired amount by repeating a cycle of "thermal denaturation→annealing(hybridization using primers)→extension reaction" while using (1) the target DNA to be amplified, (2) at least two types of oligonucleotide primers capable of specifically binding with the target DNA, (3) a buffer, (4) an enzyme, and (5) a deoxyribonucleotide triphosphate such as dATP, dCTP, dGTP or dTTP.

A description will hereinafter be made about one example of a measurement procedure making use of the real-time PCR system according to the first embodiment.

Primers of different DNA sequences designed beforehand are charged into the reaction regions A1, respectively. No particular limitation is imposed on the charging method. It is possible to rely, for example, upon a method that makes use of inkjet or the like. Solutions with the individual primers contained therein are added dropwise into the reaction regions A1, respectively, and are then dried there.

Total RNA extracted from a sample is then transcripted into cDNA by a reverse transcription method, and the cDNA is charged into the respective reaction regions A1. Additionally, a deoxynucleotide triphosphate (dNTP) as a raw material for the respective bases required for amplification, an intercalator ("SYBR™ GREEN I"), an enzyme required for the DNA extension amplification reaction (DNA polymerase or the like), and the like are also charged.

In the thermal denaturation step, the heaters 16 are set to raise the internal temperatures of the respective reaction regions A1 to 95° C. so that the double-stranded DNA is denatured into a single-stranded DNA. In the subsequent annealing step, the heaters 16 are set to lower the internal temperatures of the respective reaction regions to 55° C. so that the primers cause the single-stranded DNA to bind to its complementary base sequence. In the next DNA extension step, the heaters 16 are set to raise the internal temperatures of the respective reaction regions to 72° C. so that using the primers as starting points of DNA synthesis, a polymerase reaction is allowed to proceed to have cDNA extended.

In every temperature cycle of the above-described "95° C. (thermal denaturation)→55° C. (hybridization using the primers)→72° C. (DNA extension)", cDNA in each reaction region A1 is amplified to a 2-fold amount. By the heaters 16 arranged for the respective reaction regions A1, the temperatures inside the respective reaction regions A1 can be controlled to the designed optimal value for the primer reaction. As the primer-dependent hybridization time and the polymerase reaction time can be controlled, the formation of unnecessary reaction byproducts can also be controlled. As a consequence, the amplification rates of the gene (cDNA) in the respective reaction regions A1 can be controlled to be equal to each other, and therefore, a PCR reaction of good accuracy can be performed.

"SYBR™ GREEN I" intercalates with ds-DNA formed during the replication reaction of the DNA. This "SYBR™ GREEN I" is a material, which intercalates with ds-DNA, and by subsequent irradiation of the exciting light L2, is excited to emit fluorescence (exciting light wavelength: 497 nm, emission wavelength: 520 nm).

Upon replication of DNA by DNA polymerase, the light L1 from the light source 12 therefore advances through the exciting-light scanning plate 13 and as the exciting light 12, has the intercalated "SYBR™ GREEN I" excited to emit the fluorescence L3. The intensity of the thus-emitted fluorescence L3 is measured and quantitated at the fluorescence detector 15 in every temperature cycle. Based on the correlation between temperature cycles and their corresponding emission intensities, the amount of an initial cDNA can be determined as a gene expression level.

Figure 8:
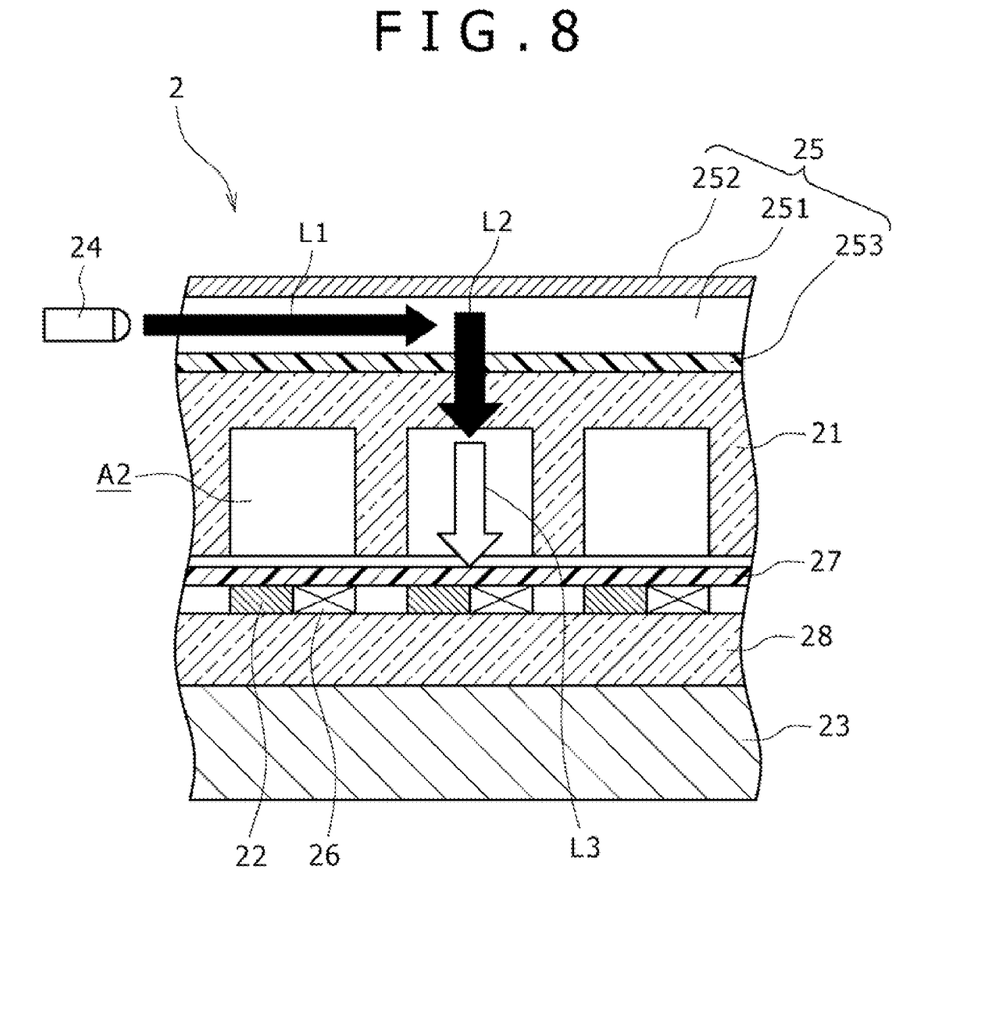
FIG. 8 is a fragmentary conceptual diagram of a second embodiment of the real-time PCR system according to the present application as viewed in side elevational cross-section.

Referring next to FIG. 8, the second embodiment of the real-time PCR system according to the present application will hereinafter be described centering around differences from the first embodiment. Concerning the elements of structure common to the first embodiment, their description is omitted herein.

This real-time PCR system 2 is common to the real-time PCR system 1 of the first embodiment in that reaction regions (wells) A2 are each provided with its own fluorescence detector 22 and heater 26. The real-time PCR system 2 is, however, different from the real-time PCR system 1 in that exciting light L2 is downwardly irradiated into a well substrate 21 and fluorescence L3 transmitted through each reaction region A2 is detected.

In the real-time PCR system 2, exciting light L1 emitted from a light source 24 is guided into each reaction region A2 via an exciting-light scanning plate 25. In the exciting-light scanning plate 25, the exciting light L1 travels through a spacer 251, and the exciting light L2 is introduced into the well substrate 21 by a reflective film 252 and a filter 253.

The exciting light L2 is irradiated onto a fluorescent material or the like on a probe in a reaction mixture in each reaction region A2 to produce the fluorescence L3. This fluorescence L3 is detected and measured by the fluorescence detector 22 arranged below the reaction region A2.

The control of the internal temperature of each reaction region A2 is effected by the heater 26 arranged below the reaction region A2, and the reaction region A2 can be constant-temperature controlled by a Peltier element 23. It is to be noted that numeral 28 indicates a measuring substrate, a filter 27, the fluorescence detectors 22 and the heaters 26 are arranged on an upper side of the measuring substrate 28, and the Peltier element 23 is arranged on a lower side of the measuring substrate 28.

In a conventional real-time PCR system, a reaction time of from 25 to 35 minutes is needed to perform the cycle of "thermal denaturation→annealing→extension reaction" approximately 30 cycles. In the course of these cycles, temperature control of approx. 2° C./sec is effected. The real-time PCR system according to the present application, on the other hand, can perform temperature control of 20° C. or higher/sec, so that time shortening as much as approx. 40 seconds or so per cycle is feasible. The entire 30 cycles can, hence, be achieved in a reaction time as short as 25 minutes or less.

As the annealing time and extension reaction time can be controlled by the designs of primers, the amplification rates in the respective reaction regions can be equally set at a constant multiplication factor (for example, twice or so). It is, therefore, possible to improve the detection accuracy of gene expression levels.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A real-time Polymerase Chain Reaction system for detecting gene expression levels, comprising:
    a plurality of reaction regions;
    a plurality of heating portions arranged corresponding to said reaction regions and having heat sources, respectively;
    an optical unit capable of irradiating exciting light of a specific wavelength to the plurality of reaction regions; and
    a plurality of fluorescence detecting portions arranged corresponding to said reaction regions, respectively,
    wherein said heating portions are each provided with a temperature detector for detecting a temperature in a vicinity of the corresponding heat source and converting said temperature into an electrical signal and a controller for controlling a thermal dose from said corresponding heat source based on a correlation between electrical signals and calorific values of said heat source stored beforehand, and
    wherein said temperature detector comprises a detection medium having diode characteristics.

2. The real-time Polymerase Chain Reaction system according to claim 1, wherein said detection medium is a thin-film transistor.

3. The real-time Polymerase Chain Reaction system according to claim 1, wherein said detection medium is an EL device.

4. The real-time Polymerase Chain Reaction system according to claim 1, wherein said controller for controlling said thermal dose from said heat source is provided with a temperature control circuit, and said detection medium is arranged in said temperature control circuit.

5. The real-time Polymerase Chain Reaction system according to claim 1, wherein said detection medium is an EL device, said controller for controlling said thermal dose from said heat source comprises a thin-film transistor as a control medium, and said EL device and said thin-film transistor are arranged in a same pixel circuit.

6. The real-time Polymerase Chain Reaction system according to claim 1, wherein said heating regions are each further provided with a Peltier element which enables constant-temperature control.

7. The real-time Polymerase Chain Reaction system according to claim 1, wherein the electrical signals in the correlation between electrical signals and calorific values of said heat source stored beforehand are selected from the group consisting of current values and voltage values.

* * * * *